US00PP26255P2

(12) United States Plant Patent
van Leeuwen

(10) Patent No.: US PP26,255 P2
(45) Date of Patent: Dec. 22, 2015

(54) ***PHLOX* PLANT NAMED 'BLIND LION'**

(50) Latin Name: *Phlox paniculata*
Varietal Denomination: Blind Lion

(71) Applicant: Jan van Leeuwen, Horst (NL)

(72) Inventor: Jan van Leeuwen, Horst (NL)

( * ) Notice: Subject to any disclaimer, the term of this patent is extended or adjusted under 35 U.S.C. 154(b) by 108 days.

(21) Appl. No.: 13/999,679

(22) Filed: Mar. 17, 2014

(51) Int. Cl.
*A01H 5/00* (2006.01)

(52) U.S. Cl.
USPC ..... Plt./320

(58) Field of Classification Search
USPC ..... Plt./320
See application file for complete search history.

(56) References Cited

PUBLICATIONS

PLUTO Paint Patent Variety Database p. 1 Jul. 22, 2015.*

* cited by examiner

*Primary Examiner* — Annette Para
(74) *Attorney, Agent, or Firm* — Penny J. Aguirre

(57) ABSTRACT

A new cultivar of *Phlox*, 'Blind Lion' that is characterized by its compact, upright plant habit and its flowers that remain in the bud stage and are dark purple in color and surrounded by dark purple bracts.

2 Drawing Sheets

Botanical classification: *Phlox paniculata.*
Cultivar designation: 'Blind Lion'.

BACKGROUND OF THE INVENTION

The present invention relates to a new and distinct cultivar of *Phlox* plant, botanically known as *Phlox paniculata* 'Blind Lion' and will be referred to hereafter by its cultivar name, 'Blind Lion'. The new cultivar represents a new herbaceous perennial grown for landscape use.

The Inventor discovered the new cultivar as a naturally occurring whole plant mutation in a trial plot in Horst, The Netherlands in June of 2011. There trial plot contained numerous named cultivars and unnamed plants of *Phlox paniculata* and therefore the parentage is unknown.

Asexual propagation of the new cultivar was first accomplished by stem cuttings in Horst, The Netherlands in the spring of 2012 by the Inventor. Asexual propagation by stem cuttings and tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blind Lion' from other varieties of *Phlox.*

1. 'Blind Lion' exhibits a compact, upright plant habit.
2. 'Blind Lion' exhibits flowers that remain in the bud stage and are dark purple in color surrounded by dark purple bracts.

'Blind Lion' is a unique *Phlox paniculata* cultivar in having flowers that remain in the bud stage. There are no other cultivars of *Phlox paniculata* known to the Inventor with this characteristic. 'Blind Lion' can be compared to the *Phlox* cultivars 'Barfourteen' (U.S. Plant Pat. No. 12,605) and 'Purple Kiss' (U.S. Plant Pat. No. 19,514). 'Barfourteen' is similar to 'Blind Lion' in having a compact plant habit (up to 45 cm in height) and in having flowers that are dark purple in color. 'Barfourteen' differs from 'Blind Lion' in having flowers that open and in having flowers with a fragrance. 'Purple Kiss' is similar to 'Blind Lion' in having a compact plant habit (up to 45 cm in height) and in having flowers that are dark purple in color. 'Purple Kiss' differs from 'Blind Lion' in having flowers that open, in having flowers with a pure white eye and in having flowers with a fragrance.

BRIEF DESCRIPTION OF THE DRAWINGS

The accompanying colored photographs illustrate the overall appearance and distinct characteristics of the new *Phlox*. The photographs were taken of a one year-old plant of 'Blind Lion' as field grown outdoors in Horst, The Netherlands and placed in a 1-gallon container for the photographs.

The photograph in FIG. 1 provides a side-view of a plant of 'Blind Lion' in bloom.

Figure 1:
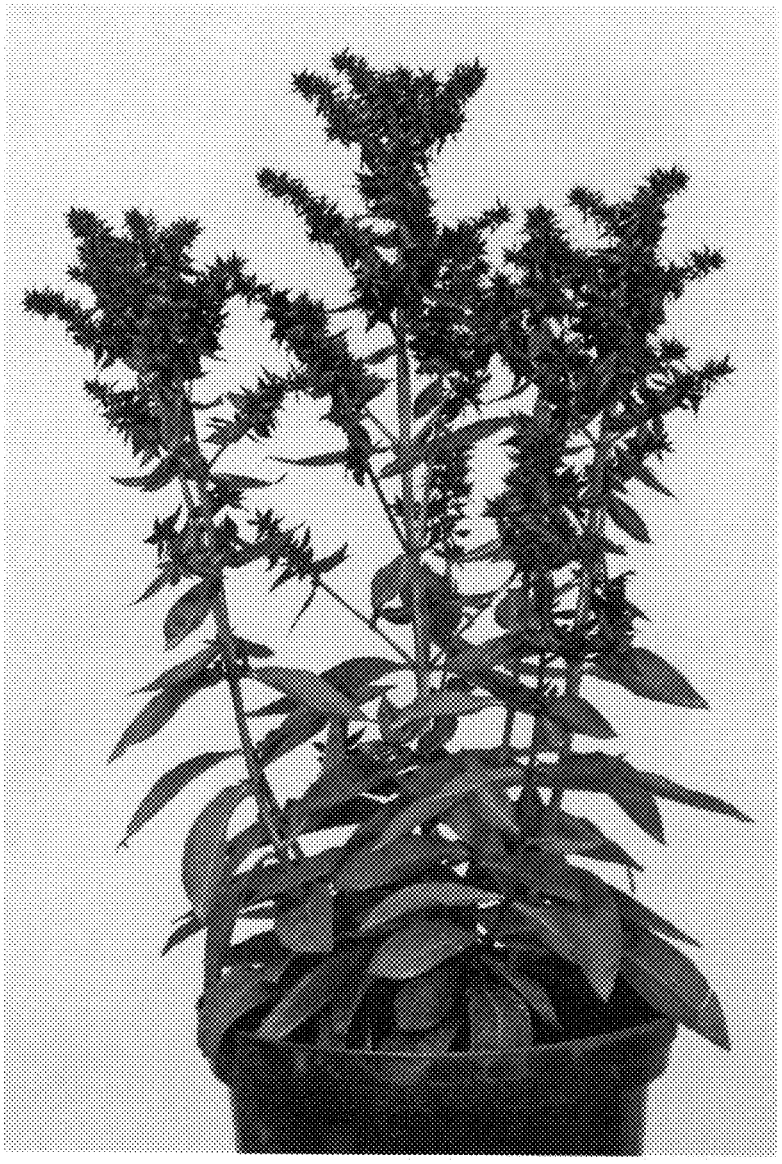
Figure 2:
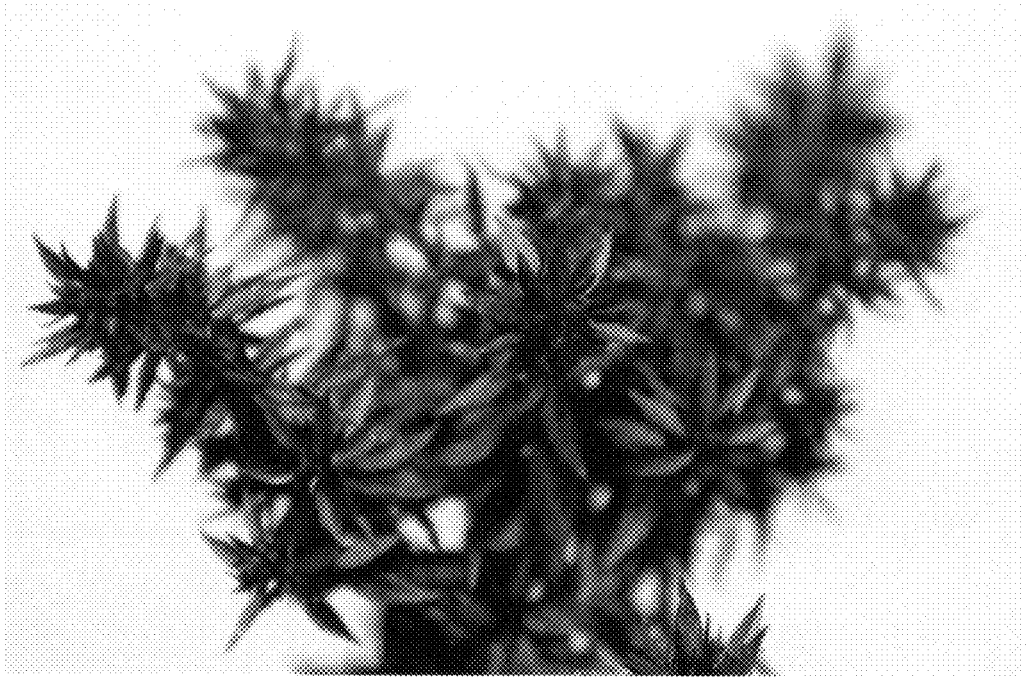

The photograph in FIG. 2 provides a close-up view of an inflorescence of 'Blind Lion' showing unopened flowers.

Figure 3:
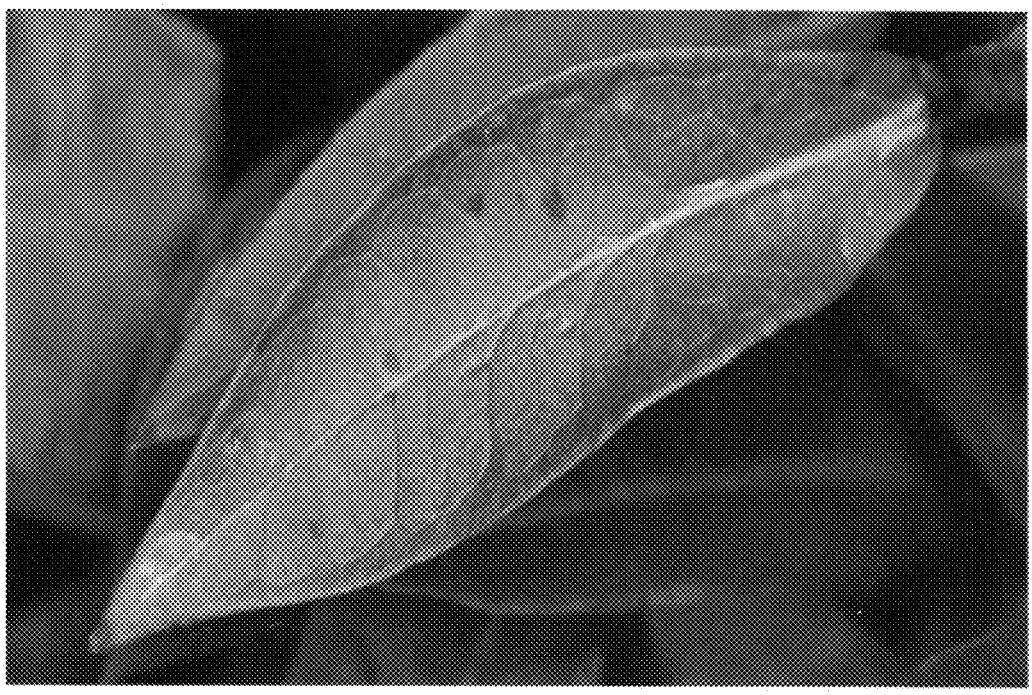

The photograph in FIG. 3 provides a close-up view of a leaf of 'Blind Lion'.

The colors in the photographs may differ slightly from the color values cited in the detailed botanical description, which accurately describe the colors of the new *Phlox.*

DETAILED BOTANICAL DESCRIPTION OF THE PLANT

The following is a detailed description of one year-old plants of the new cultivar as grown outdoors in a trial plot in Horst, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—July to October (6 to 8 weeks) in the Netherlands.

*Plant habit*.—Herbaceous perennial, compact, upright.

*Height and spread*.—An average of 38.7 cm in height and 25.8 cm spread.

*Cold hardiness*.—At least in U.S.D.A. Zone 6.

*Diseases and pests*.—No susceptibility or resistance to diseases or pests has been observed.

*Root description*.—Fine and fibrous.

*Growth rate*.—Moderate.

*Propagation*.—Stem cuttings and tissue culture.

Stem description:

*Stem size*.—Main stems; an average of 11.9 cm in length and 5 mm in diameter, lateral stems; 19.4 cm in length and 3 mm in diameter.

*Stem shape*.—Rounded.

*Stem strength*.—Strong and sturdy.

*Stem color*.—144C suffused with N186A and N186C to 187A at the nodes.

*Stem surface*.—Glabrous, moderately glossy.

*Stem aspect*.—Main stems held at an average angle of 15° to vertical, lateral stems held at an average angle of 20° to main stems.

*Internode length*.—An average of 3.3 cm.

*Branching habit*.—Flowering stems emerge from base, an average of 1 main stem per plant one year in age and 5 lateral branches.

Foliage description:

*Leaf shape*.—Narrowly obovate to narrowly elliptic and slightly carinate.

*Leaf division*.—Simple.

*Leaf base*.—Truncate.

*Leaf apex*.—Acute.

*Leaf venation*.—Pinnate, not conspicuous, 144C on upper surface and lower surface.

*Leaf margins*.—Entire and revolute.

*Leaf attachment*.—Petiolate.

*Leaf arrangement*.—Opposite.

*Leaf surface*.—Glabrous, upper surface; slightly glossy, lower surface; dull.

*Leaf color*.—Upper surface newly formed; 146A and strongly suffused with N186A to N186B, lower surface newly formed; a blend between 144A and 146B, upper surface mature; 147B, lower surface mature; 144B.

*Leaf size*.—An average of 8.4 cm in length and 2.8 cm in width.

*Leaf quantity*.—An average of 16 (8 pairs) per stem.

*Leaf fragrance*.—None.

*Petioles*.—V-shaped, an average of 3 mm in width and 2 mm in length, upper surface; 144A strongly suffused with N186C and lower surface; 144C, surface is glabrous.

Flower description:

*Inflorescence type*.—Compound terminal panicle of flower buds surrounded by showy bracts.

*Lastingness of inflorescence*.—Up to 8 weeks.

*Inflorescence size*.—An average of 19.2 cm in height and 12 cm in diameter.

*Flower fragrance*.—None.

*Flower number*.—An average of 300 per inflorescence, one inflorescence per stem.

*Flower aspect*.—Upright to outward.

*Flower bud*.—An average of 3 mm in length and 1 mm in width, narrow obovate in shape, 144B in color strongly suffused with N186C and 200A.

*Flower form*.—Numerous bracts with no reproductive organs, flowers remain in the bud stage and do not open.

*Bracts*.—An average of 5, narrow elliptic to lanceolate in shape, an average of 5 mm in length, and 2 mm in width, narrowly acute apex, cuneate base, immature and mature surface color; 203A with very lightly suffused with N186A, glabrous, moderately glossy surface.

*Sepals*.—An average of 5, narrow elliptic to lanceolate in shape, an average of 3 mm in length and 1 mm in width, acute apex, cuneate base, immature and mature surface color; 203A with very lightly suffused with N186A, glabrous, moderately glossy surface.

*Petals*.—Not described as the flowers do not open.

*Peduncles*.—Strong, primary; an average of 18 cm in length and 3.5 mm in width, secondary; an average of 9 cm in length and 2 mm in width, primary; held upright, secondary; held at an average angle of 45° to the primary, both primary and secondary; 146B and strongly suffused with N186C and 200A in color, and glabrous surface.

*Reproductive organs*.—No reproductive organs were formed; the flowers do not open.

It is claimed:

1. A new and distinct cultivar of *Phlox* plant named 'Blind Lion' as herein illustrated and described.

* * * * *